US008623132B2

(12) United States Patent
Krzysik et al.

(10) Patent No.: US 8,623,132 B2

(45) Date of Patent: Jan. 7, 2014

(54) LIQUID THICKENER FOR SURFACTANT SYSTEMS

(75) Inventors: Duane G. Krzysik, Hudson, OH (US); Virginia L. Gibson, Broadview Heights, OH (US); William J. Reiman, Macedonia, OH (US); Timothy J. Roach, Concord Township, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 13/820,846

(22) PCT Filed: Sep. 7, 2011

(86) PCT No.: PCT/US2011/050596

§ 371 (c)(1), (2), (4) Date: Jul. 17, 2013

(87) PCT Pub. No.: WO2012/033783

PCT Pub. Date: Mar. 15, 2012

(65) Prior Publication Data

US 2013/0284068 A1 Oct. 31, 2013

Related U.S. Application Data

(60) Provisional application No. 61/380,507, filed on Sep. 7, 2010.

(51) Int. Cl.

| | |
|---|---|
| ***C11D 1/74*** | (2006.01) |
| ***C11D 3/20*** | (2006.01) |
| ***C11D 3/22*** | (2006.01) |
| ***A61K 8/34*** | (2006.01) |
| ***A61K 8/60*** | (2006.01) |
| ***A61Q 19/00*** | (2006.01) |
| ***B01F 17/00*** | (2006.01) |

(52) U.S. Cl.

USPC ................. 106/287.26; 106/287.23; 106/311; 106/499; 106/504; 516/204

(58) Field of Classification Search

USPC ............... 106/287.23, 287.26, 311, 499, 504; 516/204

See application file for complete search history.

(56) References Cited

U.S. PATENT DOCUMENTS

| | | | |
|---|---|---|---|
| 5,851,541 | A | 12/1998 | Corey et al. |
| 2002/0123625 | A1 | 9/2002 | Polovsky et al. |

FOREIGN PATENT DOCUMENTS

| | | | |
|---|---|---|---|
| EP | 0987018 | A2 | 3/2000 |
| EP | 2314275 | A2 | 4/2001 |

OTHER PUBLICATIONS

Derwent-Acc-No. 2009-B49910, abstract of Chinese Patent Specification No. CN 101332160 A (Dec. 2008).*

* cited by examiner

*Primary Examiner* — Anthony J Green

(74) *Attorney, Agent, or Firm* — Thoburn T. Dunlap

(57) ABSTRACT

The present invention generally relates to blends that contain alkoxylated, lipophilic polyol compounds having about three moles of lipophilic, substituents per mole of polyol which are polyethylene glycol methyl glucose trioleate and polyethylene glycol methyl glucose dioleate and, more specifically, to the use of such compounds as thickeners in liquid surfactant compositions.

33 Claims, No Drawings

LIQUID THICKENER FOR SURFACTANT SYSTEMS

CROSS REFERENCE TO RELATED APPLICATION

This application claims priority from PCT Application Ser. No. PCT/US2011/050596 filed on Sep. 7, 2011, which claims the benefit of U.S. Provisional Application No. 61/380,507 filed on Sep. 7, 2010.

FIELD OF THE INVENTION

The present invention generally relates to blends that contain alkoxylated, lipophilic polyol compounds having about three moles of lipophilic substituents per mole of polyol and, more specifically, to the use of such compounds as thickeners in liquid surfactant compositions.

BACKGROUND OF THE INVENTION

Liquid compositions containing surfactants, for example, shampoos, dishwashing liquids and other personal care, home care and industrial products, typically contain thickeners to increase the viscosity of the liquid compositions sufficiently to enable convenient handling. Often, the thickeners comprise an alkoxylated polyol containing lipophilic substituents, for example, ethoxylated methyl glucose esterified with a fatty acid. Such thickeners are typically alkoxylated to an extent sufficient to provide water-solubility and provide viscosification to the liquid surfactant composition. The lipophilic substituent, for example, fatty acid, typically provides associative thickening characteristics to the thickener.

Often, the thickeners are introduced to the liquid surfactant compositions in solid form and mixed under conditions effective to dissolve the thickener into the liquid surfactant composition and cause significant viscosity increases, for example, up to about 2,000 to 100,000 centipoise (cP) or higher. Frequently, the mixing must be conducted at elevated temperatures in the range of about 50° C. to about 80° C. in order to promote the dissolution of the thickener and obtain the desired viscosity enhancement (known in the art as "hot processing"). However, formulators of products comprising thickened, surfactant-containing liquids, for example, shampoos, desire the ability to formulate their products at ambient temperatures generally in the range of about 20° C. to about 30° C. (known in the art as "cold processing"). Additionally, formulators also desire thickeners which can be introduced to the liquid surfactant compositions in a liquid form rather than a solid form. The ability to introduce the thickener in a liquid form can provide a formulator with a greater degree of accuracy in introducing the correct amount of thickener to the liquid surfactant system and also better facilitate automated processing.

Given the above, there is a need in the art for improved compositions suitable for use as thickeners in liquid surfactant systems. In one embodiment, the thickeners can be introduced by cold processing and in a liquid state. Methods for using compositions to thicken liquid compositions comprising surfactants are also desired.

SUMMARY OF THE INVENTION

The present invention generally relates to blends that contain alkoxylated, lipophilic polyol compounds having about three moles of lipophilic substituents per mole of polyol and, more specifically, to the use of such compounds as thickeners in liquid surfactant compositions.

In one embodiment, the present invention relates to a liquid composition comprising: (i) polyethylene glycol methyl glucose dioleate, polyethylene glycol methyl glucose trioleate, or a combination thereof; (ii) 1,3-propanediol, 1-2-propanediol, or a combination thereof; and (iii) water.

In another embodiment, the present invention relates to a liquid composition comprising: (a) from about 55 weight percent to about 75 weight percent polyethylene glycol methyl glucose dioleate, polyethylene glycol methyl glucose trioleate, or a combination thereof; (b) from about 8 weight percent to about 22 weight percent 1,3-propanediol, 1-2-propanediol, or a combination thereof; and (c) from about 15 weight percent to about 25 weight percent water.

In still another embodiment, the present invention relates to a liquid composition comprising: (I) from about 58 weight percent to about 72 weight percent polyethylene glycol methyl glucose trioleate; (II) from about 8 weight percent to about 22 weight percent 1,3-propanediol, 1-2-propanediol, or a combination thereof; and (III) from about 18 weight percent to about 22 weight percent water.

In still yet another embodiment, the present invention relates to a liquid composition comprising: (A) from about 58 weight percent to about 72 weight percent polyethylene glycol methyl glucose dioleate; (B) from about 8 weight percent to about 22 weight percent 1,3-propanediol, 1-2-propanediol, or a combination thereof; and (C) from about 18 weight percent to about 22 weight percent water.

In still yet another embodiment, the present invention relates to a liquid composition comprising: (1) polyethylene glycol methyl glucose dioleate, polyethylene glycol methyl glucose trioleate, or a combination thereof; (2) an alkylene glycol, a polyalkylene glycol, or a mixture thereof; and (3) water.

In still yet another embodiment, the present invention relates to a liquid composition comprising: (i) from about 55 weight percent to about 73 weight percent of a polyethylene glycol methyl glucose trioleate; (ii) from about 8 weight percent to about 22 weight percent of 1,3-propanediol; and (iii) from about 18 weight percent to about 22 weight percent water, or (a) from about 55 weight percent to about 73 weight percent of a polyethylene glycol methyl glucose trioleate; (b) from about 8 weight percent to about 22 weight percent of 1,2-propanediol; and (c) from about 15 weight percent to about 25 weight percent water, or (I) from about 55 weight percent to about 73 weight percent of a polyethylene glycol methyl glucose dioleate; (II) from about 8 weight percent to about 22 weight percent of 1,3-propanediol; and (III) from about 17 weight percent to about 25 weight percent water, or (A) from about 55 weight percent to about 73 weight percent of a polyethylene glycol methyl glucose dioleate; (B) from about 8 weight percent to about 22 weight percent of 1,2-propanediol; and (C) from about 17 weight percent to about 23 weight percent water.

In still yet another embodiment, the present invention relates to a liquid composition comprising: polyethylene glycol methyl glucose dioleate, polyethylene glycol methyl glucose trioleate, or a combination thereof; 1,3-propanediol, 1-2-propanediol, or a combination thereof; and water, wherein the liquid composition has a viscosity of less than about 30,000 mPa·s.

In still yet another embodiment, the present invention relates to a liquid composition comprising: polyethylene glycol methyl glucose dioleate, polyethylene glycol methyl glucose trioleate, or a combination thereof; 1,3-propanediol, 1-2-propanediol, or a combination thereof; and water, wherein the liquid composition has a turbidity of less than about 20 NTUs.

In still yet another embodiment, the present invention relates to a liquid composition comprising: polyethylene glycol methyl glucose dioleate, polyethylene glycol methyl glucose trioleate, or a combination thereof; 1,3-propanediol, 1-2-propanediol, or a combination thereof; and water, wherein the liquid composition is stable for at least 1 freeze/thaw cycle.

In still yet another embodiment, the present invention relates to a liquid composition in accordance with any mixture disclosed and discussed herein.

In still yet another embodiment, the present invention relates to a liquid composition as disclosed and discussed herein for use as a thickener in a personal care product.

DETAILED DESCRIPTION OF THE INVENTION

The present invention generally relates to blends that contain alkoxylated, lipophilic polyol compounds having about three moles of lipophilic substituents per mole of polyol and, more specifically, to the use of such compounds as thickeners in liquid surfactant compositions.

Given the above, in one embodiment alkoxylated, lipophilic polyol compounds are provided which are useful, for example, as thickeners in liquid surfactant-containing systems. In another embodiment, the alkoxylated, lipophilic polyol compounds of the present invention are dissolved in a suitable solvent to provide a liquid thickener for use in viscosifying surfactant-containing liquid compositions.

In the embodiments detailed below, although the disclosed ranges for the total amount of each component of the compositions of the present invention may individually total more than 100 weight percent when each component is taken individually and totaled using the broadest amounts disclosed herein, one of skill in the art will realize that this is not the case. While overlapping weight ranges for the various components and ingredients that can be contained in the compositions of the invention have been expressed for selected embodiments and aspects of the invention, it should be readily apparent that the specific amount of each component in the disclosed personal care, home care, and industrial care compositions will be selected from its disclosed range such that the amount of each component is adjusted so that the sum of all components in the composition will total 100 weight percent. The amounts employed will vary with the purpose and character of the desired product and can be readily determined by one skilled in the formulation art and from the literature.

In one embodiment, in the compositions of the present invention at least 5 weight percent of the polyol compound(s) have about three moles of the lipophilic substituent per mole of polyol. In this embodiment, it has been found that the presence of a sufficient portion of the polyol compounds having about three moles of the lipophilic substituent per mole of the polyol can enhance the ability of the composition to thicken a liquid surfactant system, preferably at cold processing temperatures.

In addition, the present invention provides processes for preparing the compositions which include the steps of alkoxylating the polyol with a suitable alkoxylation reagent, for example, ethylene oxide, and introducing a lipophilic substituent, for example, by esterification with a fatty acid. The processes also provide for introducing the lipophilic substituents prior to the alkoxylation step as well as sequential introductions of the lipophilic substituent and the alkoxylating reagent.

In one embodiment, the polyols suitable for use as starting materials in accordance with the present invention comprise any compounds having three or more hydroxyl groups per molecule which are reactive with the alkoxylation reagents and the lipophilic reagents described below. General examples include, but are not limited to, glycerols, polyglycerols, sugar alcohols (e.g., sorbitol or sorbitan), and saccharides (e.g., glucose and its derivatives). In another embodiment, additional examples of the polyols which can be used according to the invention include, but are not limited to, trimethylolethane[2-methyl-2-(hydroxymethyl)-1,3-propanediol], trimethylolpropane[2-ethyl-2-(hydroxy-methyl)-1,3-propanediol], pentaerythritol (2,2-dimethylol-1,3-propanediol), diglycerol (glycerol dimer), dipentaerythritol, glycerol, and the like.

In another embodiment, polyol starting materials for use in accordance with the present invention include, but are not limited to, glucose derivatives (e.g., glycosides including, but not limited to, glucosides, galactosides, monosaccharides, oligosaccharides having up to about 10 saccharide repeating units per molecule and sucrose). In still another embodiment, polyol starting materials for use in accordance with the present invention include, but are not limited to, glucosides (e.g., alkyl glucosides including, but not limited to, methyl glucoside, ethyl glucoside, propyl glucoside, butyl glucoside and amyl glucoside). Such polyols are commercially available.

Suitable reagents for alkoxylating the polyols of the present invention include, but are not limited to, alkylene oxides (e.g., ethylene oxide, propylene oxide, butylene oxide and mixtures thereof). Other alkoxylating reagents including, but not limited to, higher alkylene oxides can be used in accordance with the present invention. Alkylene oxides suitable for use in accordance with the present invention are commercially available. The amount of alkoxylation in accordance with the present invention is that which is effective to provide water solubility and viscosification in a liquid surfactant composition. Typically, such amounts range from about 50 to about 400, or from about 80 to about 180, or even from about 100 to about 160 moles of alkylene oxide per mole of polyol. Here, as well as elsewhere in the specification and claims, individual numerical values, or limits, can be combined to form additional non-disclosed and/or non-stated ranges. Methods for alkoxylating polyols, for example, by direct alkoxylation, are known to those skilled in the art and as such a detailed discussion herein is omitted for the sake of brevity. Alternatively, partially alkoxylated methyl glucosides, for example, GLUCAM™ E-20 (PEG-20 methyl glucoside) available from Lubrizol Advanced Materials, Inc., can be used as a starting material which can then be further alkoxylated to contain the desired degree of alkoxylation.

The lipophilic reagents suitable to derivatize the polyols of the present invention include any compounds which are reactive with the polyols and have sufficient molecular weight to promote associative thickening when introduced into a liquid, surfactant-containing system. Typically, the lipophilic reagents comprise hydrocarbon or substituted hydrocarbon moieties with from about 8 to about 30, or from about 12 to about 26, or even from about 16 to about 22 carbon atoms per molecule. Here, as well as elsewhere in the specification and claims, individual numerical values, or limits, can be combined to form additional non-disclosed and/or non-stated ranges. The particular structure of the lipophilic reagents is not critical to the present invention and may, for example, be alkyl, aryl, alkylaryl, alkenyl and may be cyclic, branched or straight. Typically, the reagents are fatty acids, fatty esters, epoxides, halides, glycidyl ethers, or vegetable or animal oils. The reagents typically provide either an ester or ether linkage to the polyol. Stated another way, in the case of a glucose derivative, for example, the ether or ester is typically attached to the glucose derivative indirectly through a polyoxyalkylene chain.

Examples of suitable fatty acids include, but are not limited to, natural or synthetic saturated or unsaturated acids which are linear or branched. The fatty acids can be used alone or as a mixture. Natural fatty acids include, for example, saturated or unsaturated linear fatty acids such as caproic acid, enanthic acid, caprylic acid, pelargonic acid, decanoic acid, lauric acid, myristic acid, palmitic acid, stearic acid, linolic acid, oleic acid, capric acid and undecanoic acid which are typically obtained by hydrolyzing vegetable oils and animal oils such as coconuts oils, palm oil, tallow, linseed oil and soybean oil. Examples of synthetic fatty acids, include, but are not limited to, linear or branched fatty acids prepared by oxidizing olefin polymers. It is also possible to use fatty acids derived from microorganisms such as, for example, γ-linolenic acid. Further, as the lower alkyl ester of the fatty acid, alkyl esters having 1 to 8 carbon atoms such as methyl, ethyl or propyl ester of the fatty acid described above can be used. The fatty acid esters of hexose or the alkyl glycoside thereof can be synthesized by using various known methods, including ester synthesis using lipase and the like: for example; (1) an ester exchange reaction between starting oils or fats and a hexose or its alkylglycoside, (2) an ester exchange reaction between a lower alkyl ester of a fatty acid and a hexose or its alkyl glycoside, or (3) an ester synthesis between a fatty acid and a hexose or its alkyl glycoside. In addition, a synthesis process using a fatty acid chloride and a hexose or its alkyl glycoside can also be employed.

Examples of other suitable lipophilic reagents include, but are not limited to, glycidyl ethers, for example, nonylphenylglycidyl ether or dodecylphenyl glycidyl ether, α-olefin epoxides, for examples, 1,2-epoxyhexadecane and their respective chlorohydrins, or alkyl halides, for examples, dodecylbromide, and the above-mentioned vegetable and animal oils. Halogenated products of fatty acids can also be used as the lipophilic reagent.

The amount of the lipophilic reagent used to derivatize the polyols of the present invention is preferably effective to promote associative thickening behavior of the polyol derivatives when present in a liquid surfactant composition. Typically, the average substitution level of the lipophilic substituent is about 3, for example, from about 2.5 to about 4, or from about 2.5 to about 3.9 and more preferably from about 2.8 to 3.6, moles per mole of polyol. Here, as well as elsewhere in the specification and claims, individual numerical values, or limits, can be combined to form additional non-disclosed and/or non-stated ranges. Details concerning the derivatization of polyols to comprise lipophilic substituents are known to those skilled in the art and as such are omitted herein for the sake of brevity. The average amount of lipophilic substituent per mole of polyol (referred to in the art as Degree of Substitution "DS") can be determined by any technique known to those skilled in the art, for example, by nuclear magnetic resonance spectroscopy ("NMR"). The lipophilic reagents suitable for use in accordance with the present invention are commercially available.

In accordance with one embodiment of the present invention, the alkoxylated, lipophilic polyol compounds comprise a mixture of compounds substituted with varying amounts of the lipophilic substituent depending upon the available hydroxyl groups on the polyol starting material. At least 5 percent of the polyol compounds in the composition have about three moles of the lipophilic substituent per mole of polyol. For example, in the case of an ethoxylated, esterified methyl glucoside, at least about 5 percent of the compounds are substituted with about three moles of the lipophilic substituent per mole of the methyl glucoside. Typically, at least about 25 percent, or at least about 50 percent, or even at least about 75 percent of the polyol derivatives in the composition have about three moles of the lipophilic substituent per mole of polyol. Here, as well as elsewhere in the specification and claims, individual numerical values, or limits, can be combined to form additional non-disclosed and/or non-stated ranges. Typically, the balance of the composition comprises polyol derivatives having one, two or four moles of the lipophilic substituent per mole of polyol. In one embodiment, less than about 75 percent, or less than about 50 percent, or even less than about 25 percent of the polyols in the composition comprise one, two or four moles of the lipophilic substituent per mole of polyol. Here, as well as elsewhere in the specification and claims, individual numerical values, or limits, can be combined to form additional non-disclosed and/or non-stated ranges.

In accordance with another embodiment of the present invention, the alkoxylated, lipophilic polyol compounds comprise a mixture of compounds substituted with varying amounts of the lipophilic substituent depending upon the available hydroxyl groups on the polyol starting material. At least 5 percent of the polyol compounds in the composition have about two moles of the lipophilic substituent per mole of polyol. For example, in the case of an ethoxylated, esterified methyl glucoside, at least about 5 percent of the compounds are substituted with about two moles of the lipophilic substituent per mole of the methyl glucoside. Typically, at least about 25 percent, or at least about 50 percent, or even at least about 75 percent of the polyol derivatives in the composition have about two moles of the lipophilic substituent per mole of polyol. Here, as well as elsewhere in the specification and claims, individual numerical values, or limits, can be combined to form additional non-disclosed and/or non-stated ranges. Typically, the balance of the composition comprises polyol derivatives having one, two or four moles of the lipophilic substituent per mole of polyol. In one embodiment, less than about 75 percent, or less than about 50 percent, or even less than about 25 percent of the polyols in the composition comprise one, two or four moles of the lipophilic substituent per mole of polyol. Here, as well as elsewhere in the specification and claims, individual numerical values, or limits, can be combined to form additional non-disclosed and/or non-stated ranges.

The sequence in which the alkylene oxide and lipophilic substituents are reacted onto the polyol is not critical to the present invention. In one embodiment of the invention, the alkoxylation reaction is conducted first, followed by substitution of the lipophilic substituent onto the polyol. In another embodiment of the invention, the polyol is first substituted with the lipophilic substituent followed by alkoxylation. In still yet another embodiment of the invention, the polyol is partially esterified, for example, to comprise one or two moles (on average) of the lipophilic substituent per mole of polyol, then ethoxylated, then subsequently esterified, for example, to comprise about three moles of the lipophilic substituent per mole of polyol. Alternatively, the polyol can be partially ethoxylated, esterified and then ethoxylated again to the desired level. Moreover, the starting material can be the polyol, a partially alkoxylated polyol or a polyol that is partially reacted with the lipophilic reagent, or both.

The derivatizations are typically conducted under sub-atmospheric pressure, for example, from about 0.001 to about 1.0 atmospheres, and at a temperature in the range of about 110° C. to about 180° C. for the alkoxylation step and about 120° C. to 200° C. for the lipophilic substitution step. Catalysts may or may not be used for the derivatizations. Typically, however, catalysts are employed to enhance the reaction rate. The catalysts can be acidic, basic, or neutral. In one embodiment, suitable catalysts for the alkoxylation step include, but are not limited to, Na, $NaOCH_3$, KOH, NaOH, $K_2CO_3$, $Na_2CO_3$. In one embodiment, suitable catalysts for the lipophilic substitution step include, but are not limited to, $Na_2CO_3$, KOH, NaOH, acids including p-toluenesulfonic acid ("p-TSA"), $H_2SO_4$, HCl, and others including organic titanates, for example, tetraisopropyl titanate available as Tyzor™ catalyst from DuPont Company, Wilmington, Del. Further details concerning the manufacture of alkoxylated, lipophilic polyol compounds are known to those skilled in the art and are described, for example, in U.S. Pat. Nos. 4,687,843; 5,109,127; 5,501,813; and 5,502,175, all of which are hereby incorporated by reference in their entireties.

The product produced from the derivatization reactions is typically in the form of a solid in a granulated or powdered form. The solid product is suitable for packaging and shipment to customers.

In another embodiment, the alkoxylated, lipophilic polyol derivatives of the present invention are dissolved in a suitable solvent to provide a liquid thickener suitable for use in viscosifying surfactant-containing liquid compositions. Any suitable liquid, or liquids, capable of dissolving the polyol derivatives are suitable for use in accordance with the present invention. In one embodiment, the liquids are aqueous with or without additional water miscible liquids. For example, suitable solvents include, but are not limited to, water, alkylene glycols having about 2 to about 5 carbon atoms per molecule, such as propylene glycol, ethylene glycol, butylene glycol, propanediol and butanediol. Dialkylene glycols (e.g., diethylene and dipropylene glycols) can be utilized as suitable solvents. Other solvents, such as for example, polyalkylene glycols such as CARBOWAX™ PEG and UCON™ Fluids available from Dow Chemical Company, Midland, Mich., can also be employed. When the product of the present invention is provided in a liquid form, it typically comprises from about 55 weight percent to about 75 weight percent, or from about 58 weight percent to about 72 weight percent, or from about 60 weight percent to about 70 weight percent, or even from about 62 weight percent to about 68 weight percent of the polyol derivative with the balance comprising the one or more liquid solvents and any desired additives. Here, as well as elsewhere in the specification and claims, individual numerical values, or limits, can be combined to form additional non-disclosed and/or non-stated ranges. Suitable additives include, but are not limited to, preservatives and biocides, which are generally present in minor amounts, for example, less than about 5 weight percent based on the total weight of the liquid composition.

In one embodiment, when in liquid form, the compositions of the present invention have viscosities of less than about 30,000 mPa·s, or less than about 25,000 mPa·s, or less than about 20,000 mPa·s, or less than about 15,000 mPa·s, less than about 10,000 mPa·s, or even less than about 5,000 mPa·s. Here, as well as elsewhere in the specification and claims, individual numerical values, or limits, can be combined to form additional non-disclosed and/or non-stated ranges. Brookfield rotating spindle method (all viscosity measurements reported herein are conducted by the Brookfield method whether mentioned or not): The viscosity measurements are calculated in mPa·s, employing a Brookfield rotating spindle viscometer, Model RVT (Brookfield Engineering Laboratories, Inc.), at about 20 revolutions per minute (rpm), at ambient room temperature of about 20° C. to about 25° C. (hereafter referred to as viscosity). Spindle sizes are selected in accordance with the standard operating recommendations from the manufacturer. Generally, spindle sizes are selected as follows:

| Spindle Size Number | Viscosity Range (mPa·s) |
|---|---|
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | greater than 50,000 |

The spindle size recommendations are for illustrative purposes only. The artisan of ordinary skill in the art will select a spindle size appropriate for the system to be measured.

In another embodiment, when in liquid form the compositions of the present invention have a clarity (turbidity) of less than about 20 NTUs, less than about 15 NTUs, less than about 10 NTUs, less than about 7.5 NTUs, less than about 5 NTUs, less than about 2.5 NTUs, less than about 1 NTU, or even are considered to be clear (i.e., have a turbidity of less than about 0.2 NTUs, or even a turbidity of 0 NTUs). Here, as well as elsewhere in the specification and claims, individual numerical values, or limits, can be combined to form additional non-disclosed and/or non-stated ranges.

The clarity (turbidity) of a composition is determined in Nephelometric Turbidity Units (NTU) employing a nephelometric turbidity meter (Micro 100 Turbidimeter, HF Scientific, Inc.) at ambient room temperature of about 20° C. to about 25° C. Distilled water (NTU=0) is utilized as a standard. Six dram screw cap vials (70 mm×25 mm) are filled almost to the top with test sample and centrifuged at 100 rpm until all bubbles are removed. Upon centrifugation, each sample vial is wiped with tissue paper to remove any smudges before placement in the turbidity meter. The sample is placed in the turbidity meter and a reading is taken. Once the reading stabilizes, the NTU value is recorded. The vial is given one-quarter turn and another reading is taken and recorded. This is repeated until four readings are taken. The average of the four readings is reported as the turbidity value. Compositions having an NTU value of about 50 or greater were judged hazy or turbid. Compositions having even higher NTU values and/or turbidities were judged opaque. As will be appreciated by those of skill in the art, the transition between hazy and opaque is not defined by a definitive numerical NTU value. Rather, it can be somewhat subjective based on the level of haziness which is then considered to be opaque. As such, no specific NTU value is attached to the transition from hazy to opaque in regards to the formulations of Comparative Examples of the thickener compositions detailed below.

In still another embodiment, the liquid compositions of the present invention are stable after at least 1 freeze/thaw cycle, at least 2 freeze/thaw cycles, at least 3 freeze/thaw cycles, or even 4 or more freeze/thaw cycles.

As used herein, freeze/thaw stability is determined by the following method. Initially, the method utilized herein visually compares the turbidity of a sample. It is applicable to any clear to amber colored material which can be obtained as a visually clear liquid at room temperature. It is reported as the average of the turbidity readings.

Specifically, a 6 dram glass vial is filled with the sample material and then placed in a freezer at −10° C. for 24 hours and then taken out and put into a 25° C. water bath for several hours until the vial and the sample are equilibrated to 25° C. The sample is placed in a micro 100 Turbidimeter. Next, the sample is rotated several times and readings are taken and averaged, the average number is reported. In the above test method the following equipment is utilized: (a) a Micro 100 Turbidimeter or equivalent is utilized; (b) a freezer capable of reaching −10° C.+/−2° C.; (c) 6 dram glass vials; and (d) a water bath capable of holding temperature of 25° C.+/−1° C.

Thus given the above, the stability of a sample after a freeze/thaw cycle is determined by: (1) placing a desired sample in a 6 dram glass vial; (2) placing the vial in freezer for 24 hours; (3) taking the sample out of the freezer and placing the sample in a 25° C. water bath, for several hours to equilibrate; (4) placing the glass vial in the turbidimeter, rotating the vial several times and taking readings; (5) averaging the readings and recording the number; (6) taking Brookfield Viscosity measurements to determine if such measurements have changed; and (7) recording any visual changes from the original material.

In one embodiment, when the polyol of the present invention is a glucose derivative (e.g., polyethylene glycol methyl glucose dioleate, polyethylene glycol methyl glucose trioleate, or any mixture thereof) and the present invention is a liquid composition, such a composition comprises from about 15 weight percent to about 25 weight percent water, or from about 16 weight percent to about 24 weight percent water, or from about 17 weight percent to about 23 weight percent water, or from about 18 weight percent to about 22 weight percent water, or even from about 18.5 weight percent to about 20 weight percent water. Here, as well as elsewhere in the specification and claims, individual numerical values, or limits, can be combined to form additional non-disclosed and/or non-stated ranges.

In addition to the above components, the compositions of this embodiment can further include suitable amounts of one or more additional solvents polyalkylene glycol or alkylene glycol such as propanediol (e.g., 1,2-propanediol, 1,3-propanediol). In still another embodiment, the compositions of this embodiment can further include suitable amounts of one or more additional solvents such as 1,3-propanediol such as Zemea™, available from DuPont of Wilmington, Del. In this embodiment, when present, this additional solvent is present in a range of about 8 weight percent to about 22 weight percent, or from about 10 weight percent to about 20 weight percent, or from about 12 weight percent to about 18 weight percent, or from about 14 weight percent to about 16 weight percent, or even about 15 weight percent additional solvent. Here, as well as elsewhere in the specification and claims, individual numerical values, or limits, can be combined to form additional non-disclosed and/or non-stated ranges.

In one embodiment, the compositions of the present invention are formed from a mixture of: (i) polyethylene glycol methyl glucose dioleate, polyethylene glycol methyl glucose trioleate, or a combination thereof; (ii) a 1,3-propanediol such as Zemea™; and (iii) water. In this embodiment, component (i) is present in a range of from about 55 weight percent to about 75 weight percent, or from about 58 weight percent to about 72 weight percent, or from about 60 weight percent to about 70 weight percent, or even from about 62 weight percent to about 68 weight percent. Here, as well as elsewhere in the specification and claims, individual numerical values, or limits, can be combined to form additional non-disclosed and/or non-stated ranges.

Furthermore, in this embodiment, component (ii) is present in a range of about 8 weight percent to about 22 weight percent propanediol, or from about 10 weight percent to about 20 weight percent propanediol, or from about 12 weight percent to about 18 weight percent propanediol, or from about 14 weight percent to about 16 weight percent propanediol, or even about 15 weight percent propanediol. Here, as well as elsewhere in the specification and claims, individual numerical values, or limits, can be combined to form additional non-disclosed and/or non-stated ranges.

Furthermore, in this embodiment, component (iii) is present in a range of about 15 weight percent to about 25 weight percent, or from about 16 weight percent to about 24 weight percent, or from about 17 weight percent to about 23 weight percent, or from about 18 weight percent to about 22 weight percent, or even from about 18.5 weight percent to about 20 weight percent. Here, as well as elsewhere in the specification and claims, individual numerical values, or limits, can be combined to form additional non-disclosed and/or non-stated ranges.

Given the above, the compositions of the present invention have a variety of end use applications, such as, for example, personal care applications, home care, and industrial applications. Typical personal care applications include, for example, pharmaceutical and cosmetic compositions, such as, for example, oral suspensions, mouthwashes, toothpastes, dentifrices, shampoos, conditioners, ointments, skin creams, lotions, body washes, bath and shower gels, soaps, and the like. Typical home care applications include, for example, products employed in a domestic household for surface cleaning or maintaining sanitary conditions, such as in the kitchen and bathroom (e.g., hard surface cleaners, hand and automatic dish care, toilet bowl cleaners and disinfectants), and laundry products for fabric care and cleaning (e.g., detergents, fabric conditioners, pre-treatment stain removers), and the like. Typical industrial applications include, for example, use as viscosity adjusters for general fluids handling and for surfactant applications, such as, suspension aids, adhesion promoters and coating materials.

In one aspect of the invention, the compositions of the present invention are used for thickening liquid compositions comprising one or more surfactants. Illustrative surfactants include, but are not limited to, anionics including fatty acid soaps, alkyl sulfates, alkyl ether sulfates, alkyl or aryl sulfonates, sulfosuccinates, sarcosinates, alkyl glucose esters or their alkoxylates and in particular sodium lauryl sulfate, ammonium lauryl sulfate, triethanolamine lauryl sulfate, sodium laureth sulfate, alpha olefin sulfonate, disodium laureth sulfosuccinates, triethanolamine stearate; non-ionics including methyl glucose esters or their alkoxylates, fatty acid alkanol amides, polyglycol ethers or their alkyl or aryl derivatives, hydroxylated lanolin, lanolin alcohols and in particular oleth-20, ceteareth-20, methyl glucose dioleate, methyl glucose stearate, glycerol monostearate, cocoyl diethanolamide, nonoxynal-7 and octoxynol-8; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl beta-aminopropionates, betaines, alkyl imidazolines and in particular cocoamphocarboxy glycinate, cocamidopropyl betaine and caproamphocarboxy propionate; mixtures of the above surfactant classes and individual surfactant types are also contemplated.

In one embodiment, a composition, or even a liquid composition, of the present invention is combined with a second liquid comprising a surfactant under mixing conditions in order to provide a viscosity enhancement of at least about 10 percent, at least about 20 percent, at least about 30 percent, at least about 40 percent, at least about 50 percent, at least about 75 percent, at least about 100 percent, at least about 125 percent, at least about 150 percent, at least about 175 percent, or even at least about 200 percent. Here, as well as elsewhere in the specification and claims, individual numerical values, or limits, can be combined to form additional non-disclosed and/or non-stated ranges.

In light of the disclosure contained in the text of this application, in one embodiment the present invention relates to a liquid composition comprising: (i) from about 55 weight percent to about 73 weight percent of a polyethylene glycol methyl glucose trioleate; (ii) from about 8 weight percent to about 22 weight percent of 1,3-propanediol; and (iii) from about 18 weight percent to about 22 weight percent water. In another embodiment, the amount of the trioleate component (i) in this embodiment is in the range of about 58 weight percent to about 72 weight percent, or from about 60 weight percent to about 70 weight percent, or from about 62 weight percent to about 68 weight percent, or from about 64 weight percent to about 66 weight percent, or even about 65 weight percent trioleate component (i). Here, as well as elsewhere in the specification and claims, individual numerical values, or limits, can be combined to form additional non-disclosed and/or non-stated ranges.

In another embodiment, the amount of the 1,3-diol component (ii) in this embodiment is in the range of about 10 weight percent to about 20 weight percent, or from about 12 weight percent to about 18 weight percent, or from about 14 weight percent to about 16 weight percent, or even about 15 weight percent 1,3-diol component (ii). Here, as well as elsewhere in the specification and claims, individual numerical values, or limits, can be combined to form additional non-disclosed and/or non-stated ranges. In another embodiment, the amount of the water component (iii) in this embodiment is in the range of about 18.5 weight percent to about 21.5 weight percent, or from about 19 weight percent to about 21 weight percent, or from about 19.5 weight percent to about 20.5 weight percent, or even about 20 weight percent water component (iii). Here, as well as elsewhere in the specification and claims, individual numerical values, or limits, can be combined to form additional non-disclosed and/or non-stated ranges. It should be noted that the above ranges with regard to the embodiments disclosed in this paragraph and the preceding paragraph are in addition to the ranges for various components disclosed above.

In light of the disclosure contained in the text of this application, in another embodiment the present invention relates to a liquid composition comprising: (a) from about 55 weight percent to about 73 weight percent of a polyethylene glycol methyl glucose trioleate; (b) from about 8 weight percent to about 22 weight percent of 1,2-propanediol; and (c) from about 15 weight percent to about 25 weight percent water. In another embodiment, the amount of the trioleate component (a) in this embodiment is in the range of about 58 weight percent to about 72 weight percent, or from about 60 weight percent to about 70 weight percent, or from about 62 weight percent to about 68 weight percent, or from about 64 weight percent to about 66 weight percent, or even about 65 weight percent trioleate component (a). Here, as well as elsewhere in the specification and claims, individual numerical values, or limits, can be combined to form additional non-disclosed and/or non-stated ranges.

In another embodiment, the amount of the 1,2-diol component (b) in this embodiment is in the range of about 10 weight percent to about 20 weight percent, or from about 12 weight percent to about 18 weight percent, or from about 14 weight percent to about 16 weight percent, or even about 15 weight percent 1,2-diol component (b). Here, as well as elsewhere in the specification and claims, individual numerical values, or limits, can be combined to form additional non-disclosed and/or non-stated ranges. In another embodiment, the amount of the water component (c) in this embodiment is in the range of about 16 weight percent to about 24 weight percent, or from about 17 weight percent to about 23 weight percent, or from about 18 weight percent to about 22 weight percent, or from about 19 weight percent to about 21 weight percent, or even about 20 weight percent water component (c). Here, as well as elsewhere in the specification and claims, individual numerical values, or limits, can be combined to form additional non-disclosed and/or non-stated ranges. It should be noted that the above ranges with regard to the embodiments disclosed in this paragraph and the preceding paragraph are in addition to the ranges for various components disclosed above.

In light of the disclosure contained in the text of this application, in still another embodiment the present invention relates to a liquid composition comprising: (I) from about 55 weight percent to about 73 weight percent of a polyethylene glycol methyl glucose dioleate; (II) from about 8 weight percent to about 22 weight percent of 1,3-propanediol; and (III) from about 17 weight percent to about 25 weight percent water. In another embodiment, the amount of the dioleate component (I) in this embodiment is in the range of about 58 weight percent to about 72 weight percent, or from about 60 weight percent to about 70 weight percent, or from about 62 weight percent to about 68 weight percent, or from about 64 weight percent to about 66 weight percent, or even about 65 weight percent dioleate component (I). Here, as well as elsewhere in the specification and claims, individual numerical values, or limits, can be combined to form additional non-disclosed and/or non-stated ranges.

In another embodiment, the amount of the 1,3-diol component (II) in this embodiment is in the range of about 10 weight percent to about 20 weight percent, or from about 12 weight percent to about 18 weight percent, or from about 14 weight percent to about 16 weight percent, or even about 15 weight percent 1,3-diol component (II). Here, as well as elsewhere in the specification and claims, individual numerical values, or limits, can be combined to form additional non-disclosed and/or non-stated ranges. In another embodiment, the amount of the water component (III) in this embodiment is in the range of about 18 weight percent to about 24 weight percent, or from about 19 weight percent to about 23 weight percent, or from about 20 weight percent to about 22 weight percent, or even about 21 weight percent water component (III). In still another embodiment, the amount of the water component (III) in this embodiment is in the range of about 17 weight percent to about 19 weight percent, or from about 17.5 weight percent to about 18.5 weight percent, or even about 18 weight percent water component (III). In still another embodiment, the amount of the water component (III) in this embodiment is in the range of about 21 weight percent to about 25 weight percent, or from about 21.5 weight percent to about 24.5 weight percent, or from about 22 weight percent to about 24 weight percent, or from about 22.5 weight percent to about 23.5 weight percent, or even about 23 weight percent water component (III). Here, as well as elsewhere in the specification and claims, individual numerical values, or limits, can be combined to form additional non-disclosed and/or non-stated ranges. It should be noted that the above ranges with regard to the embodiments disclosed in this paragraph and the preceding paragraph are in addition to the ranges for various components disclosed above.

In light of the disclosure contained in the text of this application, in still another embodiment the present invention relates to a liquid composition comprising: (A) from about 55 weight percent to about 73 weight percent of a polyethylene glycol methyl glucose dioleate; (B) from about 8 weight percent to about 22 weight percent of 1,2-propanediol; and (C) from about 17 weight percent to about 25 weight percent water. In another embodiment, the amount of the dioleate component (A) in this embodiment is in the range of about 58 weight percent to about 72 weight percent, or from about 60 weight percent to about 70 weight percent, or from about 62 weight percent to about 68 weight percent, or from about 64 weight percent to about 66 weight percent, or even about 65 weight percent dioleate component (A). Here, as well as elsewhere in the specification and claims, individual numerical values, or limits, can be combined to form additional non-disclosed and/or non-stated ranges.

In another embodiment, the amount of the 1,2-diol component (B) in this embodiment is in the range of about 10 weight percent to about 20 weight percent, or from about 12 weight percent to about 18 weight percent, or from about 14 weight percent to about 16 weight percent, or even about 15 weight percent 1,2-diol component (B). Here, as well as elsewhere in the specification and claims, individual numerical values, or limits, can be combined to form additional non-disclosed and/or non-stated ranges. In another embodiment, the amount of the water component (C) in this embodiment is in the range of about 18 weight percent to about 24 weight percent, or from about 19 weight percent to about 23 weight percent, or from about 20 weight percent to about 22 weight percent, or even about 21 weight percent water component (C). In still another embodiment, the amount of the water component (C) in this embodiment is in the range of about 17 weight percent to about 23 weight percent, or from about 18 weight percent to about 22 weight percent, or from about 19 weight percent to about 21 weight percent, or even about 20 weight percent water component (C). Here, as well as elsewhere in the specification and claims, individual numerical values, or limits, can be combined to form additional non-disclosed and/or non-stated ranges. It should be noted that the above ranges with regard to the embodiments disclosed in this paragraph and the preceding paragraph are in addition to the ranges for various components disclosed above.

EXAMPLES

The following examples are provided for illustrative purposes and are not intended to limit the scope of the claims which follow. In the Examples, the amounts recited are given in weight percent unless otherwise indicated. Additionally, comparative examples are marked as such.

Tables 1 and 2 below contain comparative examples of various compositions comprising: (i) polyethylene glycol methyl glucose trioleate (PEG methyl glucose trioleate); (ii) 1,3-propanediol (e.g., Zemea™); and (iii) water. These comparative examples failed as they were either too viscous, too opaque (too high an NTU value), and/or did not survive at least 1 freeze/thaw cycle without an unacceptable degradation in either the sample's viscosity and/or turbidity.

TABLE 1

| Component | Comparative Ex. 1 | Comparative Ex. 2 | Comparative Ex. 3 | Comparative Ex. 4 |
|---|---|---|---|---|
| PEG Methyl Glucose Trioleate | 50 | 50 | 60 | 60 |
| 1,3-propanediol (Zemea ™) | 25 | 20 | 15 | 10 |
| Water | 25 | 30 | 25 | 30 |
| Viscosity (MPa · s) | 38,400 | 82,200 | 81,800 | 156,600 |
| Turbidity (NTUs) | 4.77 | 4.58 | 7.99 | 6.78 |
| Free/Thaw Stability | Yes | Yes | Yes | Yes |

TABLE 2

| Component | Comparative Ex. 5 | Comparative Ex. 6 | Comparative Ex. 7 | Comparative Ex. 8 | Comparative Ex. 9 |
|---|---|---|---|---|---|
| PEG Methyl Glucose Trioleate | 60 | 65 | 70 | 70 | 75 |
| 1,3-propanediol (Zemea ™) | 10 | 20 | 15 | 20 | 10 |
| Water | 30 | 15 | 15 | 10 | 15 |
| Viscosity (MPa · s) | 156,600 | 7,000 | 8,100 | 2,560 | 40,010 |
| Turbidity (NTUs) | 6.78 | 9.5 | 13.4 | 13.5 | Opaque |
| Free/Thaw Stability | Yes | No | No | No | No |

Tables 3 and 4 below contain examples within the scope of the present invention of various compositions comprising: (i) polyethylene glycol methyl glucose trioleate (PEG methyl glucose trioleate); (ii) 1,3-propanediol (e.g., Zemea™); and (iii) water. These examples have viscosities, turbidities and freeze/thaw stability in accordance with the definitions set forth above.

TABLE 3

| Component | Example 1 | Example 2 | Example 3 |
|---|---|---|---|
| PEG Methyl Glucose Trioleate | 60 | 58.5 | 65 |
| 1,3-propanediol (Zemea ™) | 20 | 20.75 | 15 |
| Water | 20 | 20.75 | 20 |
| Viscosity (MPa · s) | 20,300 | 20,150 | 25,650 |
| Turbidity (NTUs) | 7.34 | 3.30 | 8.36 |
| Free/Thaw Stability | Yes | Yes | Yes |

TABLE 4

| Component | Example 4 | Example 5 | Example 6 |
|---|---|---|---|
| PEG Methyl Glucose Trioleate | 72.34 | 70 | 67.93 |
| 1,3-propanediol (Zemea ™) | 8.51 | 10 | 11.32 |
| Water | 19.15 | 20 | 20.75 |
| Viscosity (MPa · s) | 14,200 | 13,500 | 13,700 |
| Turbidity (NTUs) | 4.54 | 9.37 | 4.56 |
| Free/Thaw Stability | Yes | Yes | Yes |

Tables 5 and 6 below contain comparative examples of various compositions comprising: (i) polyethylene glycol methyl glucose dioleate (PEG methyl glucose dioleate); (ii) 1,3-propanediol (e.g., Zemea™); and (iii) water. These comparative examples failed as they were either too viscous, too opaque (too high an NTU value), and/or did not survive at least 1 freeze/thaw cycle without an unacceptable degradation in either the sample's viscosity and/or turbidity.

TABLE 5

| Component | Comparative Ex. 10 | Comparative Ex. 11 | Comparative Ex. 12 | Comparative Ex. 13 |
|---|---|---|---|---|
| PEG Methyl Glucose Dioleate | 40 | 55 | 60 | 65 |
| 1,3-propanediol (Zemea ™) | 10 | 10 | 10 | 20 |
| Water | 50 | 35 | 30 | 15 |
| Viscosity (MPa · s) | 85,400 | 59,200 | 30,200 | 4,600 |
| Turbidity (NTUs) | 0.73 | 0.86 | Clear | Opaque |
| Free/Thaw Stability | Yes | Yes | Yes | No |

TABLE 6

| Component | Comparative Ex. 14 | Comparative Ex. 15 | Comparative Ex. 16 |
|---|---|---|---|
| PEG Methyl Glucose Dioleate | 65 | 70 | 70 |
| 1,3-propanediol (Zemea ™) | 15 | 15 | 20 |
| Water | 20 | 15 | 10 |
| Viscosity (MPa · s) | 7,100 | 3,800 | 2,350 |
| Turbidity (NTUs) | Hazy/once Clear/twice | Clear | 283 |
| Free/Thaw Stability | No/once Yes/twice | No | No |

In light of the composition of Comparative Example 14, this example was re-run two additional times using the same weight percentages of each component as detailed in Table 6. It was discovered during the second and third runs of Comparative Example 14 that the composition disclosed therein actually falls within the scope of the present invention. While not wishing to be bound by any one explanation, it is believed that the first run of Comparative Example 14 suffered from contamination while being prepared, the source of which was eliminated in the second and third runs.

Table 7 below contains examples within the scope of the present invention of various compositions comprising: (i) polyethylene glycol methyl glucose dioleate (PEG methyl glucose dioleate); (ii) 1,3-propanediol (e.g., Zemea™); and (iii) water. These examples have viscosities, turbidities and freeze/thaw stability in accordance with the definitions set forth above.

TABLE 7

| Component | Example 7 | Example 8 | Example 9 | Example 10 |
|---|---|---|---|---|
| PEG Methyl Glucose Dioleate | 55 | 60 | 65 | 70 |
| 1,3-propanediol (Zemea ™) | 20 | 15 | 10 | 10 |
| Water | 25 | 25 | 25 | 20 |
| Viscosity (MPa · s) | 15,950 | 16,200 | 18,100 | 8,650 |
| Turbidity (NTUs) | 0.65 | Clear | 1.22 | 1.88 |
| Free/Thaw Stability | Yes | Yes | Yes | Yes |

Table 8 below contains comparative examples of various compositions comprising: (i) polyethylene glycol methyl glucose trioleate (PEG methyl glucose trioleate); (ii) 1,2-propanediol (i.e., propylene glycol); and (iii) water. These comparative examples failed as they were either too viscous, too opaque (too high an NTU value), and/or did not survive at least 1 freeze/thaw cycle without an unacceptable degradation in either the sample's viscosity and/or turbidity.

TABLE 8

| Component | Comparative Ex. 17 | Comparative Ex. 18 | Comparative Ex. 19 |
|---|---|---|---|
| PEG Methyl Glucose Trioleate | 40 | 55 | 70 |
| 1,2-propanediol (Propylene Glycol) | 10 | 10 | 20 |
| Water | 50 | 35 | 10 |
| Viscosity (MPa · s) | Too Viscous (Gel) | 114,000 | 1,400 |
| Turbidity (NTUs) | 1.25 | 3.15 | Opaque |
| Free/Thaw Stability | Yes | Yes | No |

Table 9 below contains examples within the scope of the present invention of various compositions comprising: (i) polyethylene glycol methyl glucose trioleate (PEG methyl glucose trioleate); (ii) 1,2-propanediol (i.e., propylene glycol); and (iii) water. These examples have viscosities, turbidities and freeze/thaw stability in accordance with the definitions set forth above.

TABLE 9

| Component | Example 11 | Example 12 | Example 13 | Example 14 |
|---|---|---|---|---|
| PEG Methyl Glucose Trioleate | 55 | 65 | 65 | 70 |
| 1,2-propanediol (Propylene Glycol) | 20 | 10 | 20 | 10 |
| Water | 25 | 25 | 15 | 20 |
| Viscosity (MPa · s) | 16,200 | 19,600 | 3,120 | 9,750 |
| Turbidity (NTUs) | 2.52 | 9.12 | 9.63 | 6.5 |
| Free/Thaw Stability | Yes | Yes | Yes | Yes |

Table 10 below contains comparative examples of various compositions comprising: (i) polyethylene glycol methyl glucose dioleate (PEG methyl glucose dioleate); (ii) 1,2-propanediol (i.e., propylene glycol); and (iii) water. These comparative examples failed as they were either too viscous, too opaque (too high an NTU value), and/or did not survive at least 1 freeze/thaw cycle without an unacceptable degradation in either the sample's viscosity and/or turbidity.

TABLE 10

| Component | Comparative Ex. 20 | Comparative Ex. 21 | Comparative Ex. 22 | Comparative Ex. 23 |
|---|---|---|---|---|
| PEG Methyl Glucose Dioleate | 40 | 65 | 65 | 70 |
| 1,2-propanediol (Propylene Glycol) | 10 | 10 | 20 | 20 |

TABLE 10-continued

| Component | Comparative Ex. 20 | Comparative Ex. 21 | Comparative Ex. 22 | Comparative Ex. 23 |
|---|---|---|---|---|
| Water | 50 | 25 | 15 | 10 |
| Viscosity (MPa · s) | 84,800 | 3,380 | 2,180 | NA |
| Turbidity (NTUs) | 0.93 | Opaque | Opaque | Opaque |
| Free/Thaw Stability | Yes | No | No | No |

Table 11 below contains examples within the scope of the present invention of various compositions comprising: (i) polyethylene glycol methyl glucose dioleate (PEG methyl glucose dioleate); (ii) 1,2-propanediol (i.e., propylene glycol); and (iii) water. These examples have viscosities, turbidities and freeze/thaw stability in accordance with the definitions set forth above.

TABLE 11

| Component | Example 15 | Example 16 |
|---|---|---|
| PEG Methyl Glucose Dioleate | 55 | 70 |
| 1,2-propanediol (Propylene Glycol) | 20 | 10 |
| Water | 25 | 20 |
| Viscosity (MPa · s) | 8,250 | 6,800 |
| Turbidity (NTUs) | 0.53 | 0.95 |
| Free/Thaw Stability | Yes | Yes |

Given the above, the present invention possesses a number of advantages over previously known compositions that can be utilized as thickeners. It should be noted that the present invention is not limited solely to the following stated advantages. Rather, the present invention is to be broadly construed based on the complete disclosure contained herein. One advantage of the present invention is that the compositions disclosed herein eliminate the need for the use of, or inclusion of, propylene glycol which has fallen into disfavor in the personal care field as it has been determined to be a skin irritant. Another advantage is that the compositions of the present invention have an increased solids content derived from the alkoxylated glucose derivatized portion and utilize alkylene glycols or polyalkylene glycols (e.g., 1-3-propanediol, 1,2-propanediol, or a mixture thereof) and water. The water portion of the present invention permits one to obtain the desired high solids content in conjunction with the desired viscosity, turbidity and freeze/thaw stability, as well as a low alkylene glycol content. Additionally, the reduction of the overall amount of alkylene glycol or polyalkylene glycol solvents in the compositions of the present invention yields compositions that do not negatively impact on the viscosity of the final personal care product to which the compositions of the present invention are added. As noted above, the compositions of the present invention are able to be cold processed.

While in accordance with the patent statutes the best mode and certain embodiments of the invention have been set forth, the scope of the invention is not limited thereto, but rather by the scope of the attached. As such, other variants within the spirit and scope of this invention are possible and will present themselves to those skilled in the art.

What is claimed is:

1. A liquid composition comprising:

(i) from about 55 weight percent to about 73 weight percent of a polyethylene glycol methyl glucose trioleate;

(ii) from about 8 weight percent to about 22 weight percent of 1,3-propanediol; and (iii) from about 18 weight percent to about 22 weight percent water, or (a) from about 55 weight percent to about 73 weight percent of a polyethylene glycol methyl glucose trioleate;

(b) from about 8 weight percent to about 22 weight percent of 1,2-propanediol; and (c) from about 15 weight percent to about 25 weight percent water, or (I) from about 55 weight percent to about 73 weight percent of a polyethylene glycol methyl glucose dioleate;

(II) from about 8 weight percent to about 22 weight percent of 1,3-propanediol; and (III) from about 17 weight percent to about 25 weight percent water, or (A) from about 55 weight percent to about 73 weight percent of a polyethylene glycol methyl glucose dioleate;

(B) from about 8 weight percent to about 22 weight percent of 1,2-propanediol; and (C) from about 17 weight percent to about 23 weight percent water, or (A') from about 55 weight percent to about 73 weight percent of a polyethylene glycol methyl glucose dioleate;

(B') from about 12 weight percent to about 20 weight percent of 1,2-propanediol; and (C') from about 17 weight percent to about 25 weight percent water.

2. The liquid composition of claim 1, wherein the amount of the trioleate component (i), the trioleate component (a), the dioleate component (I), or the dioleate component (A) is independently selected to be in the range of about 58 weight percent to about 72 weight percent.

3. The liquid composition of claim 1, wherein the amount of the trioleate component (i), the trioleate component (a), the dioleate component (I), or the dioleate component (A) is independently selected to be in the range of about 60 weight percent to about 70 weight percent.

4. The liquid composition of claim 1, wherein the amount of the trioleate component (i), the trioleate component (a), the dioleate component (I), or the dioleate component (A) is independently selected to be in the range of about 62 weight percent to about 68 weight percent.

5. The liquid composition of claim 1, wherein the amount of the trioleate component (i), the trioleate component (a), the dioleate component (I), or the dioleate component (A) is independently selected to be in the range of about 64 weight percent to about 66 weight percent.

6. The liquid composition of claim 1, wherein the amount of the trioleate component (i), the trioleate component (a), the dioleate component (I), or the dioleate component (A) is independently selected to be about 65 weight percent.

7. The liquid composition of claim 1, wherein the amount of the 1,3-diol component (ii), the 1,2-diol component (b), the 1,3-diol component (II), or the 1,2-diol component (A) is independently selected to be in the range of about 10 weight percent to about 20 weight percent.

8. The liquid composition of claim 1, wherein the amount of the 1,3-diol component (ii), the 1,2-diol component (b), the 1,3-diol component (II), or the 1,2-diol component (A) is independently selected to be in the range of about 12 weight percent to about 18 weight percent.

9. The liquid composition of claim 1, wherein the amount of the 1,3-diol component (ii), the 1,2-diol component (b), the 1,3-diol component (II), or the 1,2-diol component (A) is independently selected to be in the range of about 14 weight percent to about 16 weight percent.

10. The liquid composition of claim 1, wherein the amount of the 1,3-diol component (ii), the 1,2-diol component (b), the 1,3-diol component (II), or the 1,2-diol component (A) is independently selected to be about 15 weight percent.

11. The liquid composition of claim 1, wherein the amount of the water component (iii) is in the range of about 18.5 weight percent to about 21.5 weight percent.

12. The liquid composition of claim 11, wherein the amount of the water component (iii) is in the range of about 19 weight percent to about 21 weight percent.

13. The liquid composition of claim 11, wherein the amount of the water component (iii) is in the range of about 19.5 weight percent to about 20.5 weight percent.

14. The liquid composition of claim 11, wherein the amount of the water component (iii) is about 20 weight percent.

15. The liquid composition of claim 10, wherein the amount of the water component (c) is in the range of about 16 weight percent to about 24 weight percent.

16. The liquid composition of claim 15, wherein the amount of the water component (c) is in the range of about 17 weight percent to about 23 weight percent.

17. The liquid composition of claim 16, wherein the amount of the water component (c) is in the range of about 18 weight percent to about 22 weight percent.

18. The liquid composition of claim 17, wherein the amount of the water component (c) is in the range of about 19 weight percent to about 21 weight percent.

19. The liquid composition of claim 18, wherein the amount of the water component (c) is about 20 weight percent.

20. The liquid composition of claim 10, wherein the amount of the water component (III) is in the range of about 18 weight percent to about 24 weight percent.

21. The liquid composition of claim 20, wherein the amount of the water component (III) is in the range of about 19 weight percent to about 23 weight percent.

22. The liquid composition of claim 21, wherein the amount of the water component (III) is in the range of about 20 weight percent to about 22 weight percent.

23. The liquid composition of claim 22, wherein the amount of the water component (III) is about 21 weight percent.

24. The liquid composition of claim 10, wherein the amount of the water component (C) is in the range of about 18 weight percent to about 22 weight percent.

25. The liquid composition of claim 24, wherein the amount of the water component (C) is in the range of about 19 weight percent to about 21 weight percent.

26. The liquid composition of claim 25, wherein the amount of the water component (C) is about 20 weight percent.

27. The liquid composition of claim 1, wherein each of the liquid compositions independently has a viscosity of less than about 30,000 mPa·s.

28. The liquid composition of claim 1, wherein each of the liquid compositions independently has a viscosity of less than about 20,000 mPa·s.

29. The liquid composition of claim 1, wherein each of the liquid compositions independently has a turbidity of less than about 20 NTUs.

30. The liquid composition of claim 1, wherein each of the liquid compositions independently has a turbidity of less than about 10 NTUs.

31. The liquid composition of claim 1, wherein each of the liquid compositions independently is stable for at least 1 freeze/thaw cycle.

32. The liquid composition of claim 1, wherein each of the liquid compositions independently is stable for at least 2 freeze/thaw cycles.

33. A liquid composition of claim 1, wherein the liquid composition is utilized as a thickener in a personal care product.

* * * * *